US007621915B2

(12) United States Patent
Frederick et al.

(10) Patent No.: US 7,621,915 B2
(45) Date of Patent: Nov. 24, 2009

(54) ACETABULAR REAMER

(75) Inventors: Phillip Frederick, Memphis, TN (US); Stephen T. Miller, Germantown, TN (US); Russell Walter, Memphis, TN (US)

(73) Assignee: Smith & Nephew, Inc., Memphis, TN (US)

( * ) Notice: Subject to any disclaimer, the term of this patent is extended or adjusted under 35 U.S.C. 154(b) by 249 days.

(21) Appl. No.: 10/775,353

(22) Filed: Feb. 10, 2004

(65) Prior Publication Data

US 2004/0225294 A1 Nov. 11, 2004

Related U.S. Application Data

(60) Provisional application No. 60/446,239, filed on Feb. 10, 2003.

(51) Int. Cl.
*A61B 17/00* (2006.01)
(52) U.S. Cl. ....................................................... 606/80
(58) Field of Classification Search ............. 606/79–81, 606/170, 180; 30/351–353, 356
See application file for complete search history.

(56) References Cited

U.S. PATENT DOCUMENTS

| 1,923,177 A | * | 8/1933 | Tucker | 408/200 |
| 3,412,733 A | * | 11/1968 | Ross | 606/81 |
| 3,633,583 A | * | 1/1972 | Fishbein | 606/81 |
| 4,473,070 A | * | 9/1984 | Matthews et al. | 606/80 |
| 4,621,637 A | | 11/1986 | Fishbein | |
| 4,712,951 A | * | 12/1987 | Brown | 408/158 |
| 5,100,267 A | | 3/1992 | Salyer | |
| 5,116,165 A | * | 5/1992 | Salyer | 407/54 |
| 5,192,329 A | * | 3/1993 | Christie et al. | 623/22.22 |
| 5,755,719 A | * | 5/1998 | Frieze et al. | 606/81 |
| 5,775,719 A | * | 7/1998 | Holden | 280/86.75 |
| 5,976,144 A | * | 11/1999 | Fishbein et al. | 606/80 |
| 6,245,074 B1 | | 6/2001 | Allard et al. | |
| 6,245,177 B1 | * | 6/2001 | Luhmann | 156/182 |
| 6,283,971 B1 | | 9/2001 | Temeles | |
| 6,676,706 B1 | | 1/2004 | Mears et al. | |

(Continued)

FOREIGN PATENT DOCUMENTS

DE 71 13 620 U 7/1971

(Continued)

*Primary Examiner*—Thomas C Barrett
*Assistant Examiner*—James L Swiger
(74) *Attorney, Agent, or Firm*—Kilpatrick Stockton LLP (57) ABSTRACT

A reamer especially well suited for use in minimally invasive hip replacement arthroplasty. The reamer is for preparation of a requisite concave surface in the patient's acetabulum suitable for the acetabular cup member of a hip prosthesis. The reamer comprises a plurality of raised edges, or cutting teeth, for cutting bone and cartilage, and a plurality of openings through which cut fragments of bone and cartilage enter the reamer body. The bone and cartilage fragments are contained within the reamer body and periodically removed so as not to contaminate the surgical site. The reamer according to certain aspects and embodiments of the present invention is easier to insert and withdraw though a minimally invasive incision in the patients body, and, also, effectively restricts bone fragments from escaping into the surgical wound. The improved reamer according to certain aspects and embodiments of the present invention is not limited to use in minimally invasive surgery.

24 Claims, 5 Drawing Sheets

U.S. PATENT DOCUMENTS

| | | |
|---|---|---|
| 6,695,850 B2 | 2/2004 | Diaz |
| 7,220,264 B1 | 5/2007 | Hershberger |
| 2003/0050645 A1 | 3/2003 | Parker et al. |
| 2003/0220647 A1* | 11/2003 | McCallum et al. ............ 606/81 |
| 2005/0075639 A1* | 4/2005 | Lechot ........................ 606/81 |
| 2005/0216020 A1* | 9/2005 | Orton .......................... 606/80 |
| 2006/0129157 A1* | 6/2006 | Desarzens et al. ............ 606/81 |

FOREIGN PATENT DOCUMENTS

| | | |
|---|---|---|
| EP | 1582155 A1 | 10/2005 |
| WO | WO 03/065906 A2 | 8/2003 |
| WO | WO 03/092513 A1 | 11/2003 |
| WO | WO 2004/024007 A1 | 3/2004 |
| WO | WO-2004100804 | 11/2004 |
| WO | WO-2007097749 A1 | 8/2007 |

* cited by examiner

ACETABULAR REAMER

CROSS-REFERENCE TO RELATED APPLICATIONS

The present application claims the benefit of U.S. Provisional Patent Application No. 60/446,239 filed Feb. 10, 2003, which is hereby incorporated by reference in its entirety.

FIELD OF THE INVENTION

The present invention relates to instruments used for joint replacement surgery, and, more particularly, to reamers used to prepare a patient's acetabulum prior to the implantation of an acetabular cup during total hip arthroplasty.

BACKGROUND

Joint implants, also referred to as joint prostheses, joint prosthetic implants, joint replacements, or prosthetic joints, are long-term surgically implantable devices that are used to partially or totally replace diseased or damaged joints, such as a hip, a knee a shoulder, an ankle, or an elbow joint, within the musculoskeletal system of a human or an animal. Since their first introduction into clinical practice in the 1960s, joint implants improved the quality of life of many patients. Both artificial hip joints and artificial shoulder joints are generally ball and socket joints, designed to match as closely as possible the function of the natural joint. Generally, the artificial socket is implanted in one bone, and the artificial ball articulates in the socket. A stem structure attached to the ball is implanted in another of the patient's bones, securing the ball in position.

The ball and socket joint of the human hip unites the femur to the pelvis, wherein the ball-shaped head of the femur is positioned within a socket-shaped acetabulum of the pelvis. The head of the femur or ball fits into the acetabulum, forming a joint which allows the leg to move forward, backward and sideways in a wide range. The acetabulum is lined with cartilage, which cushions the bones and allows the joint to rotate smoothly and with minimal friction. An envelope of tough ligaments connects the pelvis and femur, covering the joint and stabilizing it. Cartilage also makes the joint strong enough to support the weight of the upper body and resilient enough to absorb the impact of exercise and activity. A healthy hip allows the leg to move freely within its range of motion, while supporting the upper body and absorbing the impact that accompanies certain activities.

However, various degenerative diseases and injuries may require replacement of all or a portion of a hip using synthetic materials. Prosthetic components are generally made from metals, ceramics, or plastics or combinations of them.

Total hip arthroplasty and hemi-arthroplasty are two procedures well known within the medical industry for replacing all or part of a patient's hip and have enabled hundreds of thousands of people to live fuller, more active lives. A total hip arthroplasty replaces both the femoral component and the acetabular surface of the joint, so that both a femoral prosthesis and an acetabular prosthesis are required. A hemi-arthroplasty may replace either the femoral component or the acetabular surface of the joint. The purpose of hip replacement surgery is to remove the damaged and worn parts of the hip and replace them with artificial parts, called prostheses, which will help make the hip strong, stable and flexible again.

In hip replacement surgery, commonly referred to as total hip arthroplasty, a patient's natural hip is replaced by two main components, a stem member which takes the place of the femoral head, and an acetabular cup member which takes the place of the acetabular socket.

A conventional acetabular cup member may include a cup, a cup and a liner, or in some cases only a liner, all of which may be formed in various shapes and sizes. Generally, a metal cup and a polymeric liner are used. However, the liner may be made of a variety of materials, including polyethylene, ultra high molecular weight polyethylene and ceramic materials. The cup is usually of generally hemispherical shape and features an outer, convex surface and an inner, concave surface that is adapted to receive a cup liner. The liner fits inside the cup and has a convex and concave surface. The cup liner is the bearing element in the acetabular component assembly. The convex surface of the liner corresponds to the inner concave surface of the cup or acetabulum, and the liner concave surface receives the head of a femoral component. An acetabular cup may include a highly polished inner surface in order to decrease wear.

The stem and ball portion of the prosthesis may be a femoral prosthesis that generally includes a spherical or near-spherical head attached to an elongate stem with a neck connecting the head and stem. In use, the elongate stem is located in the intramedullary canal of the femur and the spherical or near-spherical head articulates relative to the acetabular component. Femoral prostheses used in total hip arthroplasty procedures may or may not differ from an endoprosthesis used in a hemi-arthroplasty. The femoral head of each type prosthesis is generally a standard size and shape. Various cups, liners, shells, stems and other components may be provided in each type arthroplasty to form modular prostheses to restore function of the hip joint.

During a total hip replacement, the surgeon will take a number of measurements to ensure proper prosthesis selection, limb length and hip rotation. After making the incision, the surgeon works between the large hip muscles to gain access to the joint. The femur is pushed out of the socket, exposing the joint cavity. The deteriorated femoral head is removed. In order to install the acetabular cup, the surgeon must prepare the bone by reaming the acetabular socket to create a surface suitable for accepting a cup, which may be held in place by bone cement, an interference or press fit, or it may have a porous outer surface suitable for bony ingrowth. The new acetabular shell is implanted securely within the prepared hemispherical socket. The plastic inner portion of the implant is placed within the metal shell and fixed into place.

Next, the femur is prepared to receive the stem. The hollow center portion of the bone is cleaned and enlarged, creating a cavity that matches the shape of the implant stem. The top end of the femur is planed and smoothed so the stem can be inserted flush with the bone surface. If the ball is a separate piece, the proper size is selected and attached. Finally, the ball is seated within the cup so the joint is properly aligned and the incision is closed.

The ball and socket joint of the human shoulder is prepared using a procedure similar to that described above. During a shoulder replacement operation, at least a portion of the proximal section of the humeral shaft is replaced by a metal prosthesis. This prosthesis generally consists of two parts: a stem that is mounted into the medullary canal of the humerus, and a head component connected in some manner to the stem. The head component replaces the bearing surface of the humerus and articulates within the glenoid cavity of the scapula to allow movement of the shoulder.

An arthritic humeral head (ball of the joint) may be removed and replaced with a humeral prosthesis. If the glenoid socket is unaffected, a hemiarthroplasty may be performed (which means that only the ball is replaced). The humeral component is made of metal and is usually press fit, but sometimes cemented, into the shaft of the bone of the humerus.

If the glenoid is affected, but conditions do not favor the insertion of a glenoid component, a non-prosthetic glenoid arthroplasty may be performed along with a humeral hemi-arthroplasty. In this procedure, the glenoid shape and orientation are corrected, but a glenoid prosthesis is not inserted. The socket is reshaped by reaming and the prosthetic ball of the humeral component articulates with the reshaped bony socket of the glenoid.

In a total shoulder joint replacement, the glenoid bone is shaped by reaming and oriented, and then covered with a glenoid component. A small amount of bone cement is commonly used to hold the artificial glenoid socket in place.

During joint replacement surgery, such as the procedures described above, typically, a rather large incision is required to allow the surgeon adequate access to the joint in order to use the instruments needed to prepare the bones, such as femur and acetabulum, to receive the prosthetic members, and to install the prosthesis itself.

During recent years, an effort has been made to reduce the size of the suture needed to implant joint prostheses, through so-called "minimally invasive" surgery. The benefits of such surgery can be significant, given the smaller incision and less intrusive nature of the procedure, shortening both surgical time and recovery time. It has been advantageous to modify traditional implants and instruments to make them particularly suitable for use in minimally invasive surgical procedures.

Reamers are devices for reaming bone tissue during reshaping of bone, specifically, in preparation for installation of joint prostheses. Reamers may also be used in connection with various trauma situations, and so forth. Reamers may have a spherical or other shaped dome if the cavity being shaped is spherical or concave, or may have an elongated shape if the cavity being shaped is a canal. An acetabular reamer is a device for removing bone tissue from an acetabular socket of an animal or a human in preparation for installation of an acetabular component of a hip prosthesis. Acetabular reamers typically have a generally hemispherical or convex dome shape with a plurality of holes and raised edges serving as cutting teeth for removing bone and cartilage from the natural socket to form a relatively smooth, concave shaped surface that generally conforms to the hemispherical external surface of an acetabular cup. The reamers may be attached to a handle, which, when connected to the reamer, allows rotation around the access of the reamer dome. Attachments of the handle is through a bracket inside the reamer dome, or by press-fitting or welding into the back side of the reamer dome. The reamers typically used for preparation of glenoid sockets are similar to those described above for use with the preparation of a hip socket for receiving an acetabular cup. During use, the reamer is rotated either by a hand-operated or power tool, so that the cutting teeth gradually remove cartilage and bone in small pieces, which pass through the holes and are, for the most part, contained within the concave interior portion of the reamer dome and are removed upon withdrawal of the reamer from the wound. It is important to remove as many of the bone chips and other particles as possible prior to completing the surgery, since they can cause problems for the patient if allowed to remain in the joint cavity. The reamers can be used in conjunction with image guided navigational systems, or other systems for precision guiding of the reamers.

For minimally invasive hip arthroplasty, it has been discovered that traditional acetabular reamers are difficult to insert and operate through a smaller incision, due to their bulk and the existence of protruding cutting teeth on their entire outer surface. The rather large diameter of a conventional acetabular reamer damages the flesh, muscle, and other soft tissue during insertion and withdrawal of the reamer through the minimally invasive incision.

One known method to minimize the incision necessary for introduction and withdrawal of a reamer is to simply remove two opposing sides of the reamer, resulting in a reamer dome having a lower profile by virtue of its reduced diameter in one direction. A recognized disadvantage of this design is that the open sides allow chips and smaller particles of reamed bone to migrate from the interior cavity of the reamer into the wound, and must be carefully removed, thereby adding both time and risk to the overall surgical procedure.

Therefore, there is a current unrealized need for an improved reamer adapted for use in minimally invasive procedures. There is a particular unrealized need for an improved acetabular reamer adapted for use in minimally invasive procedures. An improved reamer is desired that is adapted for introduction and operation through a smaller surgical incision than conventionally available reamers. Also needed is an improved reamer that would minimally damage the flesh, muscle, and other soft tissues during insertion, operation, and withdrawal. There is a current unrealized need for an improved reamer adapted for use in minimally invasive procedures, which reliably captures the reamed bone particles, at least as well as a conventional reamer, in order to prevent the particles from falling into the wound.

In general, reamers are needed that are easy to use and manufacture, minimize tissue damage, simplify surgical procedures, are versatile, allow for faster healing with fewer complications, require less post-surgical immobilization, and are less costly to produce and operate.

SUMMARY

According to various embodiments according to the present invention, there are provided acetabular reamers especially well suited for use in minimally invasive hip arthroplasty. According to some aspects, the reamers are hollow and of a generally hemispherical, modified hemispherical or other generally convex shape. The reamers are for preparation of a requisite concave surface in a patient's acetabulum suitable for the acetabular cup member of a hip prosthesis. According to some aspects, the reamers comprise a plurality of raised edges, or cutting teeth, for cutting bone and cartilage, and a plurality of openings through which cut fragments of bone and cartilage enter the reamer body. According to some aspects, the reamers contain bone chips at least as well as a conventional reamer. The bone and cartilage fragments are contained within the reamer body and periodically removed so as not to contaminate the surgical site. Reamers according to certain aspects and embodiments of the present invention are easier to insert and withdraw though a minimally invasive incision in the patients body, and, can also effectively restrict bone fragments from escaping into the surgical wound. Reamers according to certain aspects and embodiments of the present invention are not limited to use in minimally invasive surgery and can also be suitable for use in conventional hip arthroplasty or other surgical procedures.

One aspect of the invention according to its certain embodiments relates to devices for reaming a cavity or canal for receiving a prosthesis, referred to herein as a reamer, and systems comprising such reamers. Another aspect provides methods of reaming a cavity or canal for receiving a prosthesis using a reamer.

Disclosed herein as a preferred embodiment of certain aspects or embodiments of the present invention is an improved acetabular reamer having features making it suitable for use with any total hip arthroplasty, but particularly advantageously suited for minimally invasive surgery. The reamers according to certain aspects and embodiments of the present invention are improved over conventional systems and adapted for minimally invasive surgery. The reamers according to certain aspects and embodiments of the present invention are distinguished from the conventional systems in that, in one aspect, they have a modified hemispherical, dome, or other convex shape, which is adapted to minimize at least one dimension of a reamer in its equatorial plane, or transversely to the rotational axis of the dome, without compromising its capturing ability. In another aspect, the positioning of the teeth, or cutting edges, of the reamers according to certain aspects and embodiments of the present invention, is modified as compared to conventional designs in order to reduce damage to soft tissues during insertion and operation of the reamers. Modifications and combinations of the foregoing aspects of the present invention are envisioned and fall within the scope of the present invention.

In one preferred embodiment, the reamer has a generally hemispherical, convex or domed surface with one or more sides flattened. The sides are flattened along a plane that is parallel to the central rotational axis of the dome, or along a plane that is sloping, or angled, towards the central rotational axis of the dome, inwards, in the direction of the equatorial plane of the dome. The plane generally sections less than half of the dome, not intercepting the central rotational axis of the dome. In one variation on the preferred embodiment, the two opposing sides of the dome are flattened along either essentially parallel, or inwardly sloping, planes. A distinguishing feature of the preferred embodiment is that the sides are enclosed, rather than being open, thereby maintaining the integrity of the interior cavity of the reamer so that the bone chips are contained therein during use. The reduced diameter in at least one direction along the equatorial plane of the reamer allows for significantly easier introduction and withdrawal of the reamer as compared to conventional reamers, and also allows for introduction and withdrawal through a smaller incision preferred for minimally invasive surgery.

In another preferred embodiment, the positioning of the teeth, or cutting edges, on the surface of a reamer is modified as compared to conventional designs in order to reduce damage to soft tissues during insertion and withdrawal of the reamers. Generally, in this embodiment, portions of the sides of the dome are free of the cutting edges, thereby allowing insertion of the reamer into the surgical side with minimal trauma to the soft tissues. In one variation, the reamer has a fully hemispherical or domed surface, which corresponds to a surface of rotation, with the cutting edges, or teeth, located, generally, in a band located centrally on the surface of the dome, and with no cutting teeth on a major portion of the surface of the two opposing sides of the dome. In another variation, the reamer is with a cut side, or an opening in the side, and devoid of the cutting teeth on the side of the dome that is opposing to the opening.

It is to be understood that reamers according to aspects and embodiments of the present invention are not limited to acetabular reamers or reamers for preparation of surfaces for joint prostheses. Use of the reamers according to be aspects of the present invention in any application requiring reaming of tissues, such as a bone tissue or a cartilage tissue, is envisioned and falls within the scope of the present invention.

The foregoing preferred embodiments facilitate the use of the reamer in a small incision typically used for minimally invasive surgery due to the absence of any cutting teeth along opposing sides which might damage the soft tissue during insertion and withdrawal through the incision.

The foregoing discloses preferred embodiments of the present invention, and numerous modifications or alterations may be made without departing from the spirit and the scope of the invention

PREFERRED EMBODIMENTS

For simplicity of representation, the CAD representations shown in FIGS. 2-7 do not show the cutting teeth. It is to be understood that reamers represented in these figures include cutting teeth of a generally conventional manner.

Figure 1:
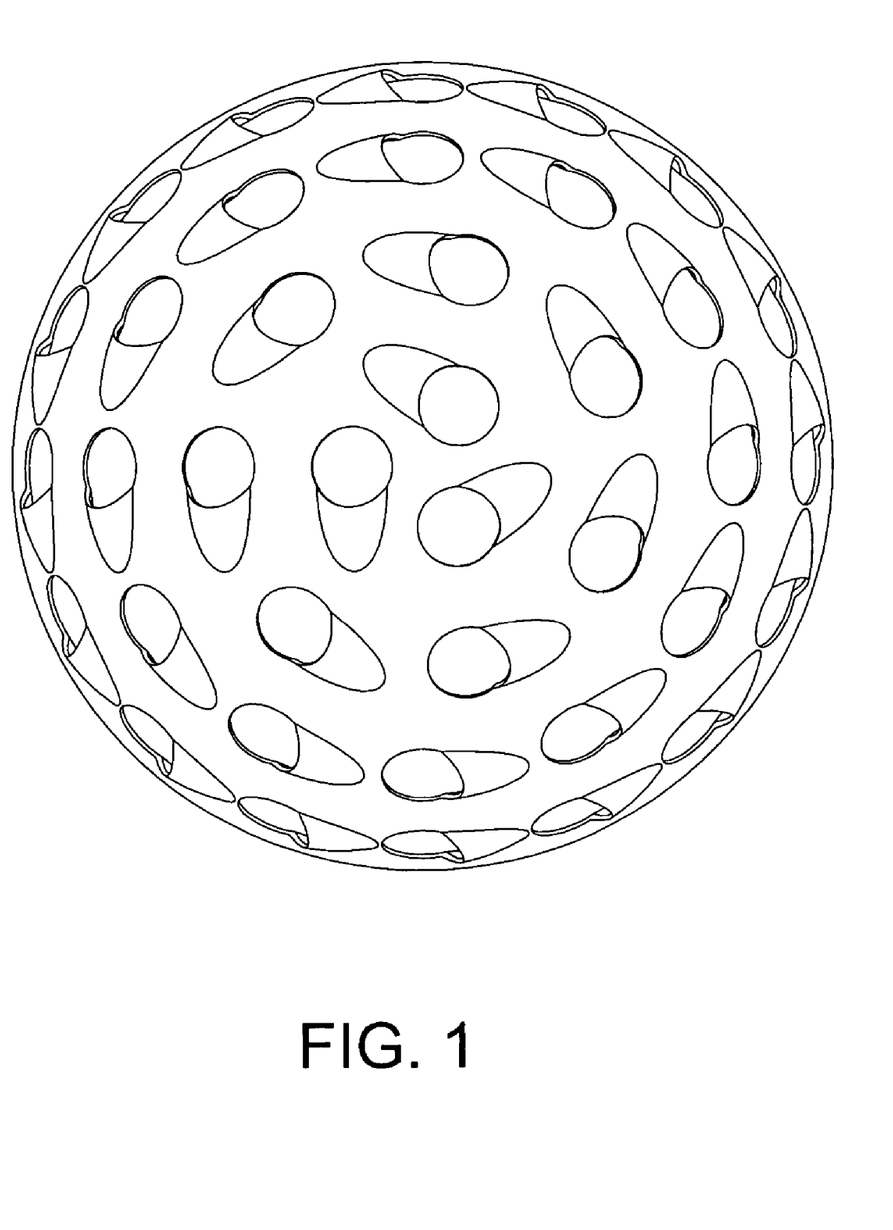
FIG. 1 is a top plan view of a conventional acetabular reamer.
Figure 2:
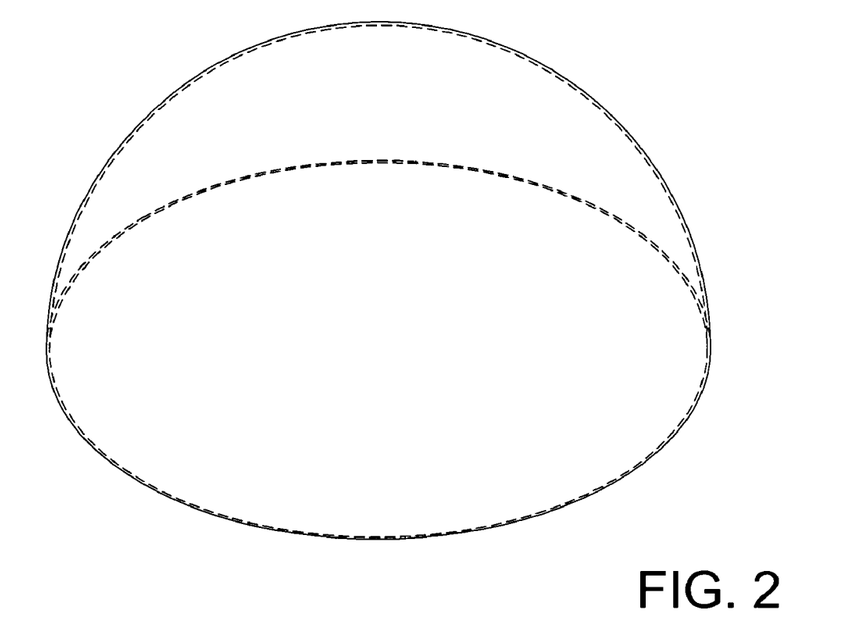
FIG. 2 is a top perspective schematic CAD view of the dome shape of a conventional acetabular reamer.

FIGS. 1 and 2 show a conventional acetabular reamer having a hemispherical, or dome, configuration, shown schematically in FIG. 2, with a plurality of projecting cutting teeth which, when the reamer is rotated, cut into the patient's acetabular socket to prepare the surface for implantation of an acetabular cup prosthesis. Each cutting tooth has a hole, or an opening, associated with it, so that, during operation of the reamer, the bone chips or particles removed by the cutting teeth of the reamer pass through the opening to the interior concave portion of the reamer, for capture and subsequent removal by a surgeon. It is commonly understood that that a variety of medical and biological problems arises when bone fragments and/or other particles are allowed to remain within the surgical site, or wound, particularly within the joint capsule, during total joint arthroplasty.

Figure 3:
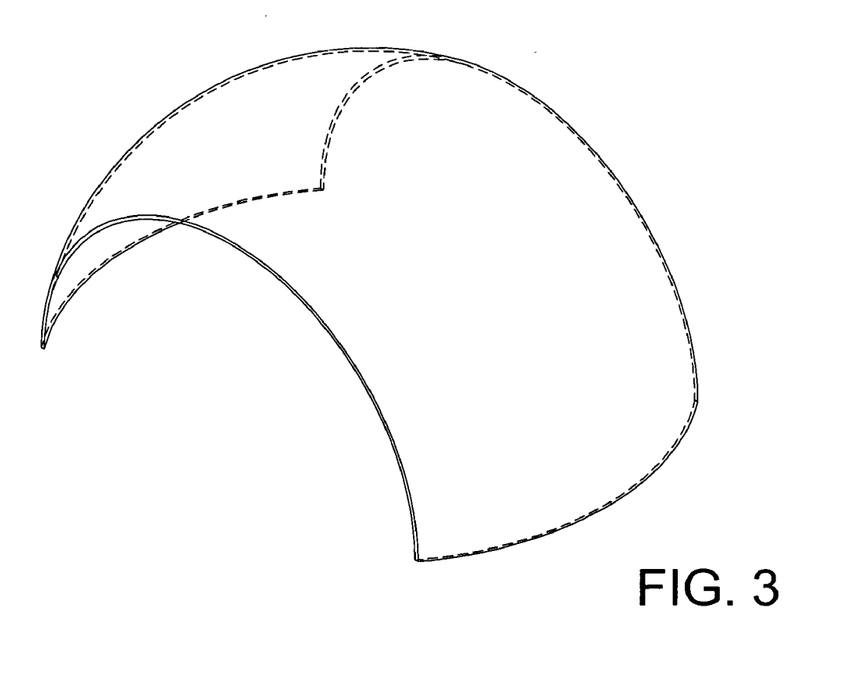
FIG. 3 is a top perspective schematic CAD view of a conventional acetabular reamer with opposing sides removed.

The conventional reamer shown in FIGS. 1 one and 2 is not well suited for minimally invasive surgery due to its relatively large diameter, or profile, across the equatorial plane, and also due to the uniform distribution, or positioning, of the cutting teeth, or edges, throughout its entire surface. Conventional reamers are difficult to insert through the relatively small opening utilized in minimally invasive surgery, and the cutting teeth frequently damage the patients' tissues, particularly soft tissue, such as skin, muscle, etc., during insertion and withdrawal of the reamer into and out of the wound. One conventional solution to this problem is to simply lower the profile, or minimize the equatorial dimension, of the reamer by simply removing opposing sides, resulting in a partial dome configuration as shown in FIG. 3. It is to be understood that a variation of conventional reamer shown in FIG. 3 has side portions removed on the opposing sides of the hemisphere, even though only one side is visible in the illustration. A primary disadvantage of this variation of the reamer is that the sides allow bone fragments to escape and migrate into the wound. Removal of the fragments takes additional time, increasing both the cost and the risk of the surgery.

Figure 4:
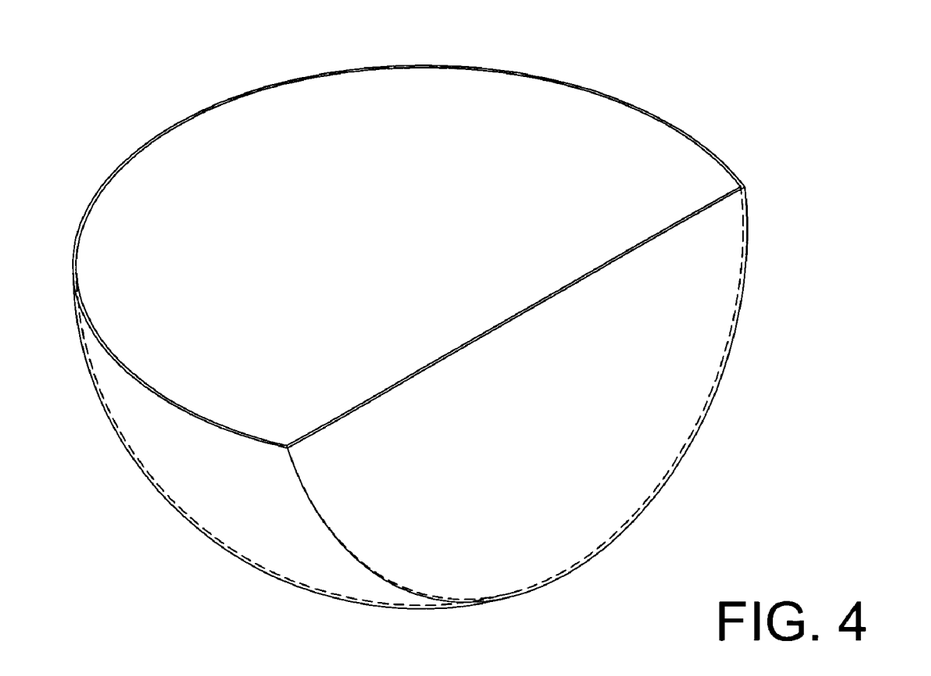
FIG. 4 is a bottom perspective schematic CAD view of an acetabular reamer according to an embodiment of the invention with one flattened side.
Figure 5:
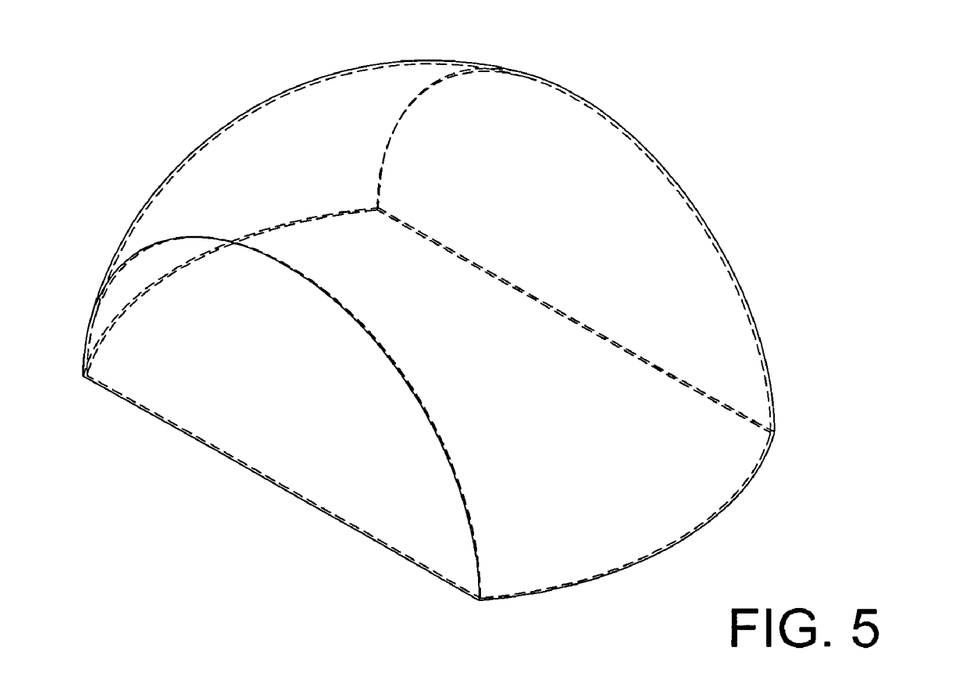
FIG. 5 is a top perspective schematic CAD view of an acetabular reamer according to an embodiment of the invention with two flattened sides.
Figure 6:
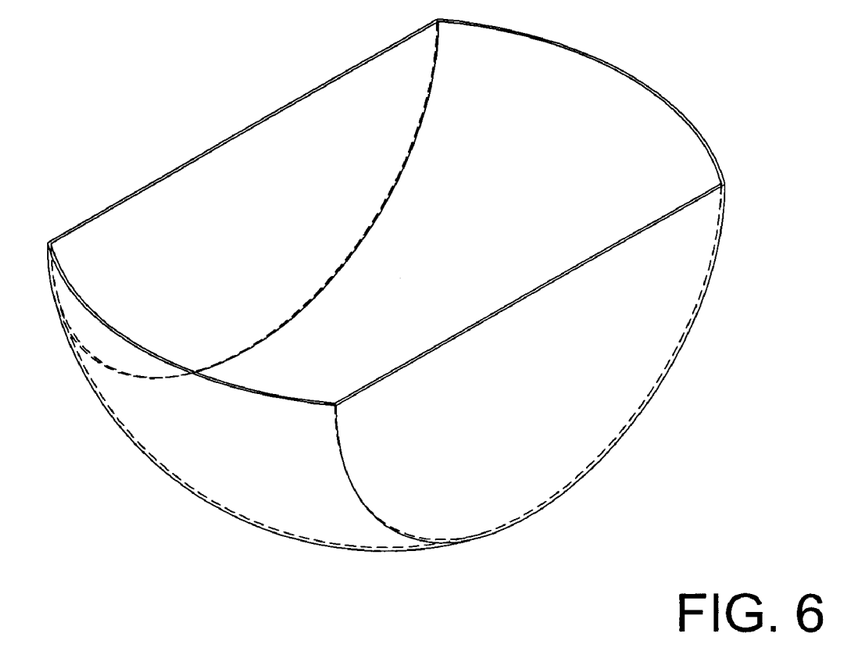
FIG. 6 is a bottom perspective schematic CAD view of an acetabular reamer with two flattened sides also shown in FIG. 4.

In order to address the aforementioned problems, in one preferred embodiment of the present invention as shown in FIGS. 4-6, the dome shape of the reamer is modified in that one or more sides of the reamer are removed, and replaced with flat side surfaces which maintain the closed nature of the interior cavity. This provides a lower profile, or dimension, of a reamer in one direction, specifically, a diameter of the dome, which facilitates insertion and withdrawal of the reamer into and from the wound. An advantage of the reamer according to this embodiment compared to a conventional reamer with removed sides, is that, unlike a reamer with removed sides, it effectively contains the bone chips in order to minimize their migration into the joint space. In a further non-limiting variation on this embodiment, it is preferred that the flat side members contain no cutting teeth in order to minimize damage to soft tissue, although cutting teeth on such surfaces may be desired for certain purposes. It is to be understood that number, shape, location and distribution of the cutting teeth on the surface of a reamer according to this embodiment of the invention varies. The backside of the dome preferably comprises an opening, as with a conventional reamer, so that particles collected within the interior may be easily disposed of after withdrawal of the reamer from the wound, but it is contemplated that the backside may be partially or completely enclosed, thereby further preventing particles from falling into the wound.

In a preferred embodiment as shown in FIGS. 4-6, the sides are flattened along a plane parallel to the central rotational axis of the dome or along a plane sloping, or angled, towards the central rotational axis of the dome inwards with respect to the equatorial plane of the dome. A plane generally sections less than half of the dome, not intercepting the central rotational axis of the dome. In one variation on the preferred embodiment illustrated in FIG. 4, one side of reamer is flat. In another variation shown in FIGS. 5 and 6, the two opposing sides of the dome are flat. When the two opposing sides are flat, they are directed either along essentially parallel or inwardly sloping planes.

In another preferred embodiment of the present invention, the problem of minimizing tissue damage during the insertion and withdrawal of the reamer into and from the surgical site, is addressed by modifying the positioning or location of the teeth, or cutting edges, on the surface of a reamer as compared to conventional designs. Generally, in this embodiment, portions of the sides of the dome are left free of the cutting edges in order to minimize tissue damage during insertion and withdrawal of the reamer. More specifically, in this preferred embodiment, the one or more sides of the reamer do not possess the cutting edges.

Figure 7:
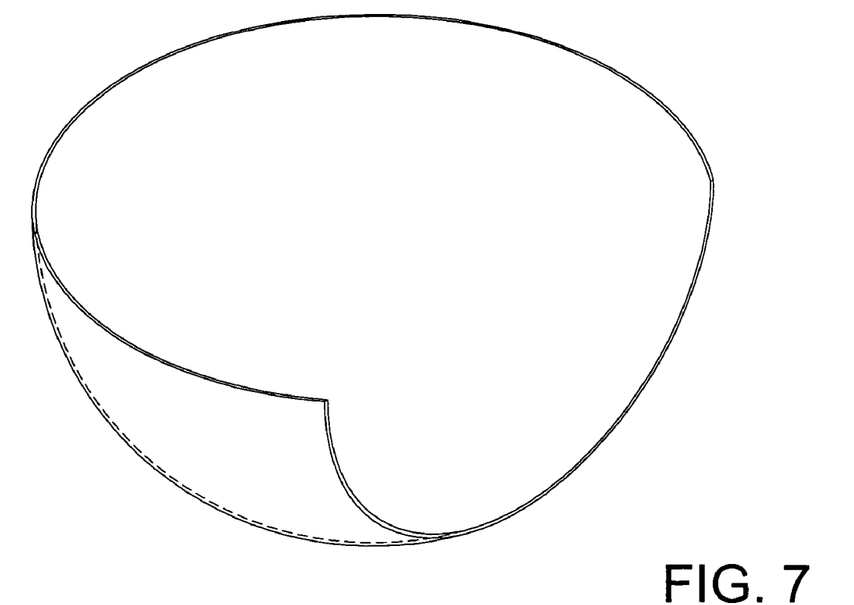
FIG. 7 is a bottom perspective schematic CAD view of an acetabular reamer according to an embodiment of the invention with one side removed.

In one variation of this preferred embodiment illustrated in FIG. 7, the reamer includes one cut side, or an opening in one side, and with the side of the dome opposing to the cut side devoid of the cutting edges. Similarly to the embodiments discussed above, the opening provides a lower profile, of a reamer, or smaller dimension in at least one direction across the equatorial plane, which facilitates insertion and withdrawal of the reamer into and from the wound. However, compared to a conventional reamer with two removed sides, the reamer with one cut side more effectively contains the bone chips, thereby minimizing their migration into the surgical space.

Figure 8:
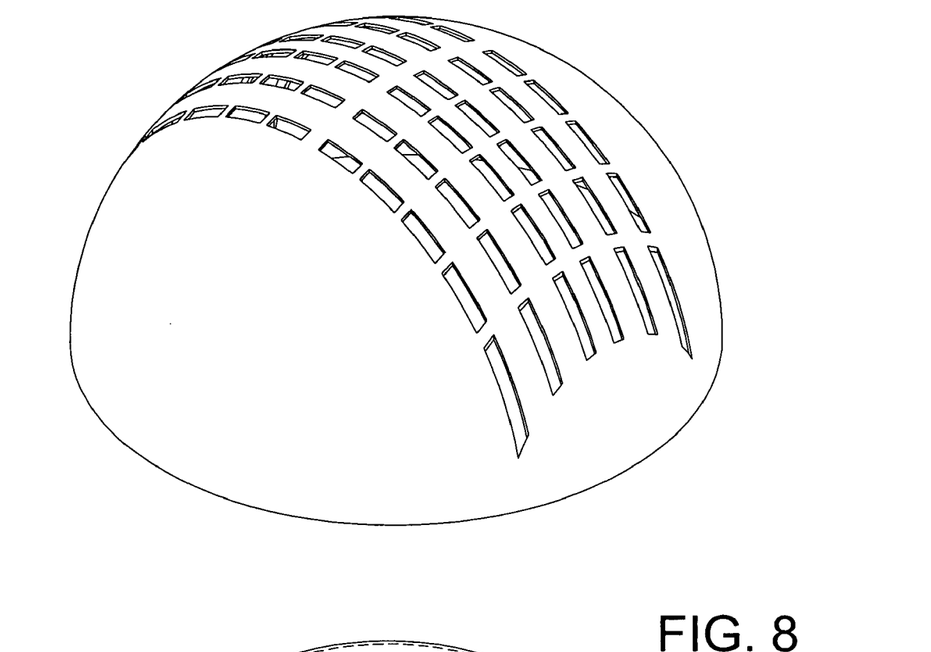
FIG. 8 is a top perspective schematic CAD view of an acetabular reamer according to an embodiment of the invention with teeth in the middle portion.
Figure 9:
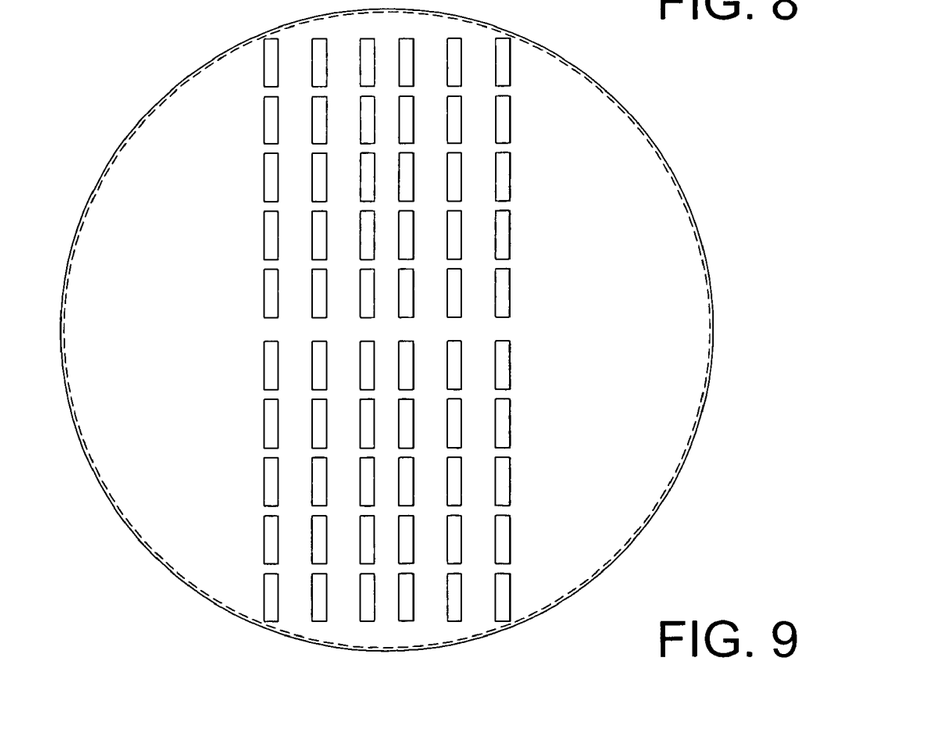
FIG. 9 is a top plan schematic CAD view of the reamer of FIG. 6.

In another variation on this preferred embodiment, illustrated in FIGS. 8 and 9, the reamer has a fully domed surface, which can be hemispherical, with no cutting teeth on a major portion of the surface on two opposing sides of the dome. Elongated cutting teeth and associated slots are positioned in a band straddling the middle portion of the dome, leaving opposing sides smooth and free of any cutting teeth. Any configuration of cutting teeth can be used, so long as they are located in a portion, portions, sector or sectors of the surface which occupy substantially less than one half of the surface area of the surface. The reamer according to this variation of the embodiment has the advantage of improved insertion and withdrawal, preferably through a smaller incision, without damaging soft tissue due to the smooth opposing sides. Simultaneously, the reamer retains the structural integrity and fragment containing ability of the fully dome surface. As with the previous embodiment, this embodiment preferably comprises an opening in the backside so that the captures particles may be easily dumped out and disposed of, but it is contemplated that the backside may be partially or completely enclosed in some instances.

Various variations on the reamers according to preferred embodiments of the present invention are envisioned and fall within the scope of the present invention. In one example, in order to minimize the diameter of the reamer, one or more sides of the reamer may be less curved or rounded that the middle portion of the dome. That is, the sides are not flattened to a plane, but remain rounded, however, a dimension of the reamer in at least one direction along the equatorial plane is reduced. In another example, one or more sides of the dome are removed and a mesh or another material covers the one or more sides.

In general, it is to be understood that shape of reamers according to aspects and embodiments of the present invention can vary, and is modified in accordance with a particular application for which the reamer is used. Incorporation of various useful features by the reamers according to aspects and embodiments of the present invention and their use in conjunction with various devices and systems is envisioned and falls within the scope of the present invention. It is also to be understood that advantageous and distinguishing features according to embodiments of the present invention can be present in a reamer in various combinations.

In one of its aspects, the present invention also provides methods of removing tissues, including bone tissues, using the reamers according to embodiments of the present invention. Specifically, the present invention provides a method of preparing an acetabular cup of a patient during hip replacement surgery. A method of removing bone using the reamers according to embodiments of the present invention comprises attaching the reamer to a handle, inserting the reamer into a bone removal site, positioning the reamer, reaming the bone with the reamer, and removing the reamer from the site of bone removal.

According to other aspects, reamers according to aspects of the invention are used to conduct joint replacement surgery such as hip replacement surgery. In such processes can include any or all of attaching the reamer to a handle, inserting the reamer into a bone removal site, positioning the reamer, reaming the bone with the reamer, and removing the reamer from the site of bone removal, inserting an acetabular prosthetic component, preparing the femur as required, inserting a femoral stem, and completing the surgery.

The particular embodiments of the invention have been described for clarity, but are not limiting of the present invention. Those of skill in the art can readily determine that additional embodiments and features of the invention are within the scope of the appended claims and equivalents thereto.

What is claimed is:

1. A reamer for reaming a bone or a cartilage, or a combination thereof, during surgery, wherein the reamer includes a hollow body comprising an exterior surface and a rim, the exterior surface of the hollow body comprising a first portion and at least one second portion, the first portion of the exterior surface of the hollow body dimensioned substantially as a surface of rotation about a rotational axis, and comprising a plurality of raised edges for cutting the bone or the cartilage or the combination thereof, and a plurality of openings for passing of fragments of the bone or the cartilage or the combination thereof into an interior of the hollow body, and the at least one second portion forming at least one generally planar exterior surface of the hollow body that extends substantially close to the rim of the reamer so as to capture fragments of the bone or the cartilage or the combination thereof into the interior of the hollow body, wherein the raised edges are confined to the first portion of the exterior surface of the hollow body, and wherein the first portion of the exterior surface of the hollow body includes a peripheral edge that forms at least a portion of a first arc, and wherein an intersection of the first portion and the at least one second portion forms a second arc that extends continuously from one point on the peripheral edge of the first portion to another point on the peripheral edge of the first portion.

2. The reamer of claim 1, wherein the at least one second portion is oriented in a plane substantially parallel to the rotational axis.

3. The reamer of claim 1, including two second portions.

4. The reamer of claim 3, wherein the two second portions are located in planes substantially parallel to one another.

5. The reamer of claim 1, wherein the surgery is a hip replacement arthroplasty and the bone and the cartilage are the acetabulum of an animal or a human.

6. A reamer for reaming a bone or a cartilage, or a combination thereof, during surgery, wherein the reamer includes a hollow body of a general dome shape comprising a generally dome-shaped exterior surface, the generally dome-shaped exterior surface of the hollow body comprising a first portion and at least one second portion, wherein the first portion of the generally dome-shaped exterior surface of the hollow body comprises a plurality of raised edges for cutting the bone or the cartilage or the combination thereof and a plurality of openings for passing of fragments of the bone or the cartilage or the combination thereof into an interior of the hollow body, the raised edges comprising a lip configured to capture fragments of the bone or cartilage or the combination thereof and to direct those fragments through the openings into the interior of the hollow body, wherein the raised edges are confined to an area of the first portion in a band straddling a middle portion of the generally dome-shaped exterior surface of the hollow body, and wherein the at least one second portion forms a portion of the dome-shaped exterior.

7. The reamer of claim 6, wherein the first portion of the generally dome-shaped exterior surface of the hollow body occupies substantially less than half of the hollow body exterior surface.

8. The reamer of claim 6, wherein the surgery is a hip replacement arthroplasty and the bone and the cartilage are in the acetabulum of an animal or a human.

9. A reamer for reaming a bone or a cartilage, or a combination thereof, during surgery, comprising a hollow dome comprising an exterior surface, the exterior surface of the hollow dome comprising a first portion and at least one second portion, the first portion of the exterior surface of the hollow dome dimensioned substantially as a surface of rotation about a rotational axis and comprising a plurality of raised edges for cutting the bone or the cartilage or the combination thereof, and a plurality of openings for passing of fragments of the bone or the cartilage or the combination thereof into an interior of the hollow dome, the raised edges comprising a lip configured to capture fragments of the bone or cartilage or the combination thereof and to direct those fragments through the openings into the interior of the hollow dome, the at least one second portion forming at least one generally planar exterior surface of the hollow dome, wherein the raised edges are confined to the first portion of the exterior surface of the hollow dome.

10. The reamer of claim 9, wherein the at least one second portion substantially encloses the hollow dome.

11. A reamer for reaming a bone or a cartilage, or a combination thereof, during surgery, comprising a generally dome-shaped hollow body, the body comprising an exterior surface comprising a first portion and at least one second portion, the first portion of the generally dome-shaped hollow body dimensioned substantially as a surface of rotation about a rotational axis, and comprising a plurality of raised edges for cutting the bone or the cartilage or the combination thereof, and a plurality of openings for passing of fragments of the bone or the cartilage or the combination thereof into an interior of the generally dome-shaped hollow body, the raised edges comprising a lip configured to capture fragments of the bone or cartilage or the combination thereof and to direct those fragments through the openings into the interior of the generally dome-shaped hollow body, the at least one second portion forming at least one generally planar exterior surface of the generally dome-shaped hollow body, wherein the raised edges are confined to the first portion of the exterior surface of the generally dome-shaped hollow body.

12. The reamer of claim 11, wherein the at least one second portion of the generally dome-shaped hollow body substantially encloses the hollow body.

13. A reamer for reaming a bone or a cartilage, or a combination thereof, during surgery, wherein the reamer comprises a hollow dome comprising an exterior surface, the exterior surface comprising a first portion and at least one second portion, wherein the first portion of the exterior surface of the hollow dome comprises a plurality of raised edges for cutting the bone or the cartilage or the combination thereof, and a plurality of openings for passing of fragments of the bone or the cartilage or the combination thereof into an interior of the hollow dome, the raised edges comprising a lip configured to capture fragments of the bone or cartilage or the combination thereof and to direct those fragments through the openings into the interior of the hollow dome, wherein the raised edges are confined to an area of the first portion in a band straddling a middle portion of the exterior surface of the hollow dome, and wherein the at least one second portion forms a portion of the exterior surface of the hollow dome.

14. The reamer of claim 13, wherein the at least one second portion is substantially enclosed.

15. The reamer of claim 13, wherein the first portion of the exterior surface of the hollow dome occupies substantially less than half of the hollow dome exterior surface.

16. A reamer for reaming a bone or a cartilage, or a combination thereof, during surgery, wherein the reamer comprises a generally dome-shaped hollow body, the hollow body comprising an exterior surface comprising a first portion and at least one second portion, wherein the first portion of the exterior surface of the generally dome-shaped hollow body comprises a plurality of raised edges for cutting the bone or the cartilage or the combination thereof, and a plurality of openings for passing of fragments of the bone or the cartilage or the combination thereof into an interior of the generally dome-shaped hollow body, the raised edges comprising a lip configured to capture fragments of the bone or cartilage or the combination thereof and to direct those fragments through the openings into the interior of the generally dome-shaped hollow body, wherein the raised edges are confined to an area of the first portion in a band straddling a middle portion of the exterior surface of the generally dome-shaped hollow body, and wherein the at least one second portion forms a portion of the exterior surface of the generally dome-shaped hollow body.

17. The reamer of claim 16, wherein the at least one second portion of the exterior surface of the generally dome-shaped hollow body substantially encloses the hollow body.

18. The reamer of claim 16, wherein the first portion of the exterior surface of the generally dome-shaped hollow body occupies substantially less than half of the exterior surface of the generally dome-shaped hollow body.

19. A reamer for reaming a bone or a cartilage, or a combination thereof, during surgery, wherein the reamer includes a hollow body, the hollow body comprising a rim and an exterior surface comprising a first portion and at least one second portion, the first portion of the exterior surface of the hollow body dimensioned substantially as a surface of rotation about a rotational axis, and comprising a plurality of raised edges for cutting the bone or the cartilage or the combination thereof, and a plurality of openings for passing of fragments of the bone or the cartilage or the combination thereof into the interior of the hollow body, the at least one second portion forming at least one generally planar exterior surface of the hollow body that extends substantially close to the rim of the reamer so as to capture fragments of the bone or the cartilage or the combination thereof into the interior of the hollow body, wherein the raised edges are confined to the first portion of the exterior surface of the hollow body, and wherein the first portion of the exterior surface of the hollow body includes a peripheral edge that forms at least a portion of a first arc, and wherein an intersection of the first portion and the at least one second portion forms a second arc that extends continuously from one point on the peripheral edge of the first portion to another point on the peripheral edge of the first portion, and where the at least one second portion of the exterior surface of the hollow body substantially encloses the hollow body.

20. A reamer for reaming a bone or a cartilage, or a combination thereof, during surgery, wherein the reamer includes a hollow body of a general dome shape, the hollow body comprising a generally dome-shaped exterior surface, the generally dome-shaped exterior surface of the hollow body comprising a first portion and at least one second portion, wherein the first portion of the generally dome-shaped exterior surface of the hollow body comprises a plurality of raised edges for cutting the bone or the cartilage or the combination thereof, and a plurality of openings for passing of fragments of the bone or the cartilage or the combination thereof into the interior of the hollow body, the raised edges comprising a lip configured to capture fragments of the bone or cartilage or the combination thereof and to direct those fragments through the openings into the interior of the hollow body, wherein the raised edges arc confined to an area of the first portion in a band straddling a middle portion of the generally dome-shaped exterior of the hollow body, and wherein the at least one second portion forms a portion of the dome-shaped exterior surface, and wherein the at least one second portion substantially encloses the hollow body.

21. A reamer for reaming a bone or a cartilage or a combination thereof, during surgery, wherein the reamer includes a cup-shaped hollow body generally formed as a section of a dome portion or as a truncated dome portion, the hollow body comprising a dome-shaped exterior surface and an open end and a substantially closed end to define an interior volume that is spatially hounded by:

(a) a first portion of the dome-shaped exterior surface comprising a plurality of raised edges for cutting the bone or the cartilage or the combination thereof, and a plurality of openings for passing of fragments of the bone or the cartilage or combination thereof into the interior volume of the hollow body, the raised edges comprising a lip configured to capture fragments of the bone or cartilage or the combination thereof and to direct those fragments through the openings into the interior volume of the hollow body, and (b) at least one second portion of the dome-shaped exterior surface that intersects with the first portion, wherein the at least one second portion has no raised edges for cutting the bone or the cartilage or the combination thereof or openings for passing of fragments of the bone or the cartilage or combination thereof into the interior volume of the hollow body, and wherein, in use, the at least one second portion generally serves to maintain the fragments of bone or cartilage or the combination thereof within the interior volume of the hollow body.

22. The reamer of claim 21, wherein the dome-shaped exterior surface is a spheroidal, ellipsoidal, or spherical exterior surface.

23. A reamer for reaming a bone or a cartilage or a combination thereof, during surgery, wherein the reamer includes a cup-shaped hollow body generally formed as a section of a dome portion or as a truncated dome portion, the hollow body comprising an exterior surface and an open end and a substantially closed end to define an interior volume that is spatially bounded by:
  (a) a first portion on the exterior surface dimensioned substantially as a surface of rotation about a rotational axis comprising a plurality of raised edges for cutting the bone or the cartilage or the combination thereof, and a plurality of openings for passing of fragments of the bone or the cartilage or combination thereof into the interior volume of the hollow body, the raised edges comprising a lip configured to capture fragments of the bone or cartilage or the combination thereof and to direct those fragments through the openings into the interior volume of the hollow body, and
  (b) at least one second portion on the exterior surface that intersects with the first portion,
  wherein, in use, the at least one second portion is configured to maintain the fragments of bone or cartilage or the combination thereof within the interior volume of the hollow body, and
  wherein the raised edges are confined to an area of the first portion in a band straddling a middle portion of the exterior surface of the cup-shaped hollow body.

24. The reamer of claim 23, wherein the exterior surface is a spheroidal, spherical, or ellipsoidal surface.

* * * * *